US006403303B1

(12) United States Patent
Shipman et al.

(10) Patent No.: US 6,403,303 B1
(45) Date of Patent: Jun. 11, 2002

(54) METHOD AND REAGENTS FOR TESTING FOR MUTATIONS IN THE BRCA1 GENE

(75) Inventors: Robert Shipman, Mississauga; James Leushner, North York; James M. Dunn, Scarborough, all of (CA)

(73) Assignee: Visible Genetics Inc., Toronto (CA)

( * ) Notice: Subject to any disclaimer, the term of this patent is extended or adjusted under 35 U.S.C. 154(b) by 0 days.

(21) Appl. No.: 08/649,950

(22) Filed: May 14, 1996

(51) Int. Cl.$^7$ .......................... C12Q 1/68; C12P 19/34; C07H 21/04
(52) U.S. Cl. .................. 435/6; 435/91.2; 536/24.33
(58) Field of Search ................ 435/6, 91.2; 536/23.1, 536/24.3, 24.33

(56) References Cited

U.S. PATENT DOCUMENTS

| 5,545,527 A | * | 8/1996 | Stevens et al. | 435/6 |
| 5,550,020 A | * | 8/1996 | Gaillie et al. | 435/6 |
| 5,622,829 A | * | 4/1997 | King et al. | 435/6 |
| 5,654,155 A | * | 8/1997 | Murphy et al. | 435/6 |
| 5,693,473 A | * | 12/1997 | Shattuck-Eidens et al. | 435/6 |

FOREIGN PATENT DOCUMENTS

| EP | 0699754 | 3/1996 |
| WO | 9302212 | 2/1993 |
| WO | 9519369 | 7/1995 |
| WO | 9633271 | 10/1996 |

OTHER PUBLICATIONS

Xu et al. Mutation Research 288 (1993) 237–248.*
Kozlowski et al. NAR (1996) 24(6): 1177–1178.*
Gayther et al. Am J of Hum Genet. 58: 451–456, 1996.*
Kozlowski et al. NAR 24: 1177–1178, 1996.*
Rossiter et al. In Polymerase Chain Reaction: A Practical Approach, Chapter 5, Oxford University Press, 1991.*
Miki et al., "A Strong Candidate for the Breast and Ovarian Cancer Susceptibility Gene BRCA1" *Science* 226: 66–71 (1994).
Struewing et al., "Detection of Eight BRCA1 Mutations in 10 Breast/Ovarian Cancer Families, Including 1 Family with Male Breast Cancer", *Am J. Hum. Genet..* 57: 1–7 (1995).
Shattuck–Eidens et al., "A Collaborative Survey of 80 Mutations in the BRCA1 Beast and Ovarian Cancer Susceptibility Gene", *J. Amer. Med. Asssoc.* 273: 535–541 (1995).
Simard, et al., "Common Origins of BRCA1 Mutations in Canadian breast and ovarian ccancer families" *Nature Genetics* 8: 3920398 (1994).
Rao, V. B.,"Direct–Sequencing of Polymerase Chain Reaction–Amplified DNA", *Anal Biochem*, 216: 1–14 (1994).
Kretz et al., "Cycle Sequencing" in *PCR Methods and Applications* 3: S107–S112 (1994).
Reeve et al., "A Novel Thermostable Polymerase for DNA Sequencing," *Nature* 376: 796–797 (1995).
Wiemann et al., "Simultaneous On–Line DNA Sequencing on Both Strands with Two Fluorescent Dyes", *Anal. Biochem.* 224: 117–121 (1995).

* cited by examiner

*Primary Examiner*—Lisa B. Arthur
(74) *Attorney, Agent, or Firm*—Oppedahl & Larson LLP

(57) ABSTRACT

Samples are tested for mutations in the BRCA1 gene using a hierarchical approach. First, each sample is amplified in one or more multiplex PCR amplification reactions. Each multiplex PCR reaction produces a mixture of amplified fragments. The sizes and amounts of these fragments are evaluated and compared to standard values reflecting the sizes and amounts of fragments produced when the same multiplex amplification is performed on the wild-type BRCA1 gene. Differences between the observed fragment sizes and/or amounts and those for the wild-type gene are indicative of a mutation with the BRCA1 gene of the sample. Next, one or more of the exons of the BRCA1 gene are sequenced, preferably only for those samples where no mutation was detected by analysis of the multiplex PCR fragments. The sequencing procedure can be performed by amplification and sequencing of the multiplex amplification mixture.

27 Claims, 3 Drawing Sheets

SEQUENCE LISTING (1) GENERAL INFORMATION:

(iii) NUMBER OF SEQUENCES: 77

(2) INFORMATION FOR SEQ ID NO: 1:

(i) SEQUENCE CHARACTERISTICS:
      (A) LENGTH: 21
      (B) TYPE: nucleic acid
      (C) STRANDEDNESS: double
      (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
      (A) ORGANISM: human (ix) FEATURE:
      (D) OTHER INFORMATION: amplification primer for BRCA1 gene (xi) SEQUENCE DESCRIPTION: SEQ ID NO:1:

GGTAGCCCCT TGGTTTCCGT G (2) INFORMATION FOR SEQ ID NO: 2:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:2:

ACGCCAGTAC CCCAGAGCAT C                    21

(2) INFORMATION FOR SEQ ID NO: 3:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:3:

AATGATGAAA ATGAAGTTGT C                    21

(2) INFORMATION FOR SEQ ID NO: 4:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:4:

GTTCATTTGC ATAGGAGATA A                    21

(2) INFORMATION FOR SEQ ID NO: 5:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:5:

GAGCCTCATT TATTTTCTTT T                                              21

(2) INFORMATION FOR SEQ ID NO: 6:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:6:

TGAAGGACAA AAACAAAAGC T                                              21

(2) INFORMATION FOR SEQ ID NO: 7:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:7:

ACCTTAAATT TTTCAACAGC T                                              21

```
(2) INFORMATION FOR SEQ ID NO: 8:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:8:

CTCTACAGAA AACACAAAAT T                                         21

(2) INFORMATION FOR SEQ ID NO: 9:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:9:

GCCTTTTGAG TATTCTTTCT A                                         21

(2) INFORMATION FOR SEQ ID NO: 10:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:10:

TTCTACTTTT CCTACTGTGG T                                         21
```

```
(2) INFORMATION FOR SEQ ID NO: 11:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
         (A) ORGANISM: human (ix) FEATURE:
         (D) OTHER INFORMATION: amplification primer for BRCA1 gene (xi) SEQUENCE DESCRIPTION: SEQ ID NO:11:

AGGTTTTCTA CTGTTGCTGC A                                              21

(2) INFORMATION FOR SEQ ID NO: 12:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
         (A) ORGANISM: human (ix) FEATURE:
         (D) OTHER INFORMATION: amplification primer for BRCA1 gene (xi) SEQUENCE DESCRIPTION: SEQ ID NO:12:

CAGCACTTCA CTCTCATTCT T                                              21

(2) INFORMATION FOR SEQ ID NO: 13:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
         (A) ORGANISM: human (ix) FEATURE:
         (D) OTHER INFORMATION: amplification primer for BRCA1 gene (xi) SEQUENCE DESCRIPTION: SEQ ID NO:13:

CATACATTTT TCTCTAACTG C                                              21
```

```
(2) INFORMATION FOR SEQ ID NO: 14:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:14:

GAAGAAGAAG AAAACAAATG G                                           21

(2) INFORMATION FOR SEQ ID NO: 15:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:15:

AGGAGGAAAA GCACAGAACT G                                           21

(2) INFORMATION FOR SEQ ID NO:16:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:16:

TACTTAAAAA ACCTGAGACC C                                           21
```

(2) INFORMATION FOR SEQ ID NO: 17:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:17:

CAAGTACATT TTTTTAACCC T                                                      21

(2) INFORMATION FOR SEQ ID NO:18:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:18:

AAAGAGAGAA ACATCAATCC   T                                        21

(2) INFORMATION FOR SEQ ID NO: 19:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:19:

TTTGACAGTT CTGCATACAT G                                                      21

(2) INFORMATION FOR SEQ ID NO: 20:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:20:

CAAATGGTCT TCAGAATAAT C                      21

(2) INFORMATION FOR SEQ ID NO: 21:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:21:

CTCCAAGGTG TATGAAGTAT G                      21

(2) INFORMATION FOR SEQ ID NO: 22:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:22:

CAGCCTTTTC TACATTCATT C                      21

```
(2) INFORMATION FOR SEQ ID NO:23:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:23:

ATTACAGCAT GAGAACAGCA G                                              21

(2) INFORMATION FOR SEQ ID NO: 24:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:24:

GAGTCATCAG AACCTAACAG T                                              21

(2) INFORMATION FOR SEQ ID NO: 25:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:25:

ATAGCAGCAT TCAGAAAGTT A                                              21
```

(2) INFORMATION FOR SEQ ID NO: 26:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:26:

TCAGTAACAA ATGCTCCTAT A                      21

(2) INFORMATION FOR SEQ ID NO:27:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:27:

CTCCCCAACT TAAGCCATGT A                      21

(2) INFORMATION FOR SEQ ID NO:28:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:28:

TCGAGTGATT CTATTGGGTT A                      21

(2) INFORMATION FOR SEQ ID NO:29:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:29:

TGGTCATGAG AATAAAACAA A                  21

(2) INFORMATION FOR SEQ ID NO: 30:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:30:

TGGCATTTGG TTGTACTTTT T                  21

(2) INFORMATION FOR SEQ ID NO: 31:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:31:

AAGCCCACCT AATTGTACTG A                  21

(2) INFORMATION FOR SEQ ID NO: 32:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:32:

TTTGGGGTCT TCAGCATTAT T                                       21

(2) INFORMATION FOR SEQ ID NO: 33:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:33:

AAGAAGAGAA ACTAGAAACA G                                       21

(2) INFORMATION FOR SEQ ID NO: 34:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:34:

AATGGATACT TAAAGCCTTC T                                       21

(2) INFORMATION FOR SEQ ID NO: 35:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:35:

AAGGGACTAA TTCATGGTTG T                               21

(2) INFORMATION FOR SEQ ID NO: 36:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:36:

GTCTGTACAG GCTTGATATT A                               21

(2) INFORMATION FOR SEQ ID NO: 37:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:37:

TGAATGTGAA CAAAAGGAAG A                               21

(2) INFORMATION FOR SEQ ID NO: 38:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:38:

ATGGGAAAAA GTGGTGGTAT A                                                        21

(2) INFORMATION FOR SEQ ID NO: 39:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:39:

AACGAAACTG GACTCATTAC T                                                        21

(2) INFORMATION FOR SEQ ID NO: 40:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:40:

TGTTTCTACC TAGTTCTGCT T                                                        21

(2) INFORMATION FOR SEQ ID NO: 41:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:41:

TGGGCTCCAG TATTAATGAA A                      21

(2) INFORMATION FOR SEQ ID NO: 42:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:42:

TCAGCAAAAC TAGTATCTTC C                      21

(2) INFORMATION FOR SEQ ID NO: 43:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:43:

CATGCATCTC AGGTTTGTTC T                      21

```
(2) INFORMATION FOR SEQ ID NO: 44:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:44:

TATGCCTAGT AGACTGAGAA G                                        21

(2) INFORMATION FOR SEQ ID NO: 45:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:45:

GCTTCCCTGC TTCCAACACT T                                        21

(2) INFORMATION FOR SEQ ID NO: 46:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:46:

TGCCTCATTT GTTTGGAAGA A                                        21
```

```
(2) INFORMATION FOR SEQ ID NO: 47:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:47:

ACAGTGCAGT GAATTGGAAG A                                         21

(2) INFORMATION FOR SEQ ID NO: 48:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:48:

CTCCCCAAAA GCATAAACAT T                                         21

(2) INFORMATION FOR SEQ ID NO: 49:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:49:

GCGTTTATAG TCTGCTTTTA C                                         21
```

(2) INFORMATION FOR SEQ ID NO: 50:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:50:

TTGGAGTGGT ATTCTTTTAA G                                            21

(2) INFORMATION FOR SEQ ID NO: 51:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:51:

TATTTCATTT TCTTGGTACC A                                            21

(2) INFORMATION FOR SEQ ID NO: 52:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:52:

ATAAAGGGGA AGGAAAGAAT T                                            21

```
(2) INFORMATION FOR SEQ ID NO: 53:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:53:

GAATTATCAC TATCAGAACA A                                              21

(2) INFORMATION FOR SEQ ID NO: 54:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:54:

CAATCAGAGT TCAATATAAA T                                              21

(2) INFORMATION FOR SEQ ID NO: 55:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:55:

CCAGCAAGTA TGAAATGTCC T                                              21
```

```
(2) INFORMATION FOR SEQ ID NO: 56:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:56:

CTTTATGTAG GATTCAGAGT A                                               21

(2) INFORMATION FOR SEQ ID NO: 57:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:57:

CTTAACAGAG ACCAGAACTT T                                               21

(2) INFORMATION FOR SEQ ID NO: 58:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:58:

TTTCCAGAAT GTTGTTAAGT C                                               21
```

(2) INFORMATION FOR SEQ ID NO: 59:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:59:

CTAGTATTCT GAGCTGTGTG C                                               21

(2) INFORMATION FOR SEQ ID NO: 60:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:60:

CCTCGCCTCA TGTGGTTTTA T                                              21

(2) INFORMATION FOR SEQ ID NO: 61:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:61:

CTCTTTAGCT TCTTAGGACA G                                              21

(2) INFORMATION FOR SEQ ID NO: 62:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:62:

CTCAAGACTC AAGCATCAGC A                            21

(2) INFORMATION FOR SEQ ID NO: 63:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE:no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:63:

TGTGAATCGC TGACCTCTCT A                            21

(2) INFORMATION FOR SEQ ID NO: 64:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:64:

AAGTGGTGCA TTGATGGAAG G                            21

(2) INFORMATION FOR SEQ ID NO: 65:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:65:

TCTCTTATCC TGATGGGTGT G                                              21

(2) INFORMATION FOR SEQ ID NO:66:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:66:

ATACAGAGTG GTGGGGTGAG A                                              21

(2) INFORMATION FOR SEQ ID NO: 67:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:67:

CAGTGGTGCG ATCTCAGCTC A                                              21

(2) INFORMATION FOR SEQ ID NO: 68:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:68:

AAGGCTGGTG CTGGAACTCT G                     21

(2) INFORMATION FOR SEQ ID NO: 69:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:69:

TAGAGGGCCT GGGTTAAGTA T                     21

(2) INFORMATION FOR SEQ ID NO: 70:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:70:

GAGAAGACTT CTGACGCTAC C                     21

(2) INFORMATION FOR SEQ ID NO: 71:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:71:

CCTACTTTGA CACTTTGAAT G                                 21

(2) INFORMATION FOR SEQ ID NO: 72:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:72:

AATGTGCCAA GAACTGTGCT A                                 21

(2) INFORMATION FOR SEQ ID NO: 73:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:73:

TAATCTCTGC TTGTGTTCTC T                                 21

(2) INFORMATION FOR SEQ ID NO: 74:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:74:

GTAGCCAGGA CAGTAGAAGG A                                                  21

(2) INFORMATION FOR SEQ ID NO: 75:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:75:

AAACCTTCCA AATCTTCAAA T                                                  21

(2) INFORMATION FOR SEQ ID NO: 76:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:76:

TTCTGTTCAT TTGCATAGGA G                                                  21

-continued (2) INFORMATION FOR SEQ ID NO: 77:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for BRCA1 gene (xi) SEQUENCE DESCRIPTION: SEQ ID NO:77:

TGTAAGGTCA ATTCTGTTCA T                                        21

METHOD AND REAGENTS FOR TESTING FOR MUTATIONS IN THE BRCA1 GENE

This application is related to U.S. patent application Ser. No. 08/271,946 filed Jul. 8, 1994, now U.S. Pat. No. 5,547,527, which is incorporated herein by reference.

BACKGROUND OF THE INVENTION

Genetic testing to determine the presence of or a susceptibility to a disease condition offers incredible opportunities for improved medical care, and the potential for such testing increases almost daily as ever increasing numbers of disease-associated genes and/or mutations are identified. One such disease-associated gene is the BRCA1 gene. Mutations in the BRCA1 gene have been shown to be linked to breast and ovarian cancer. Miki et al., "A Strong Candidate for the Breast Cancer and Ovarian Cancer Susceptibility Gene BRCA1", Science 226: 66–71 (1994).

Since the identification of the BRCA1 gene, researchers have tested many individuals using sequencing, single-stranded conformational polymorphism, allele-specific oligonucleotide hybridization and heteroduplex analysis to identify BRCA1 mutations in families with a history of breast and ovarian cancer. Shattuck-Eidens et al., "A Collaborative Survey of 80 Mutations in the BRCA1 Breast and Ovarian Cancer Susceptibility Gene", *J. Amer. Med. Assoc.* 273: 535–541 (1995). Diagnostic screening to identify persons with these mutations, and thus with an apparent genetic predisposition to breast and ovarian cancers offers the opportunity for increased monitoring of high-risk patients which should lead to earlier detection of cancer. Such early detection improves the likelihood of successful treatment and the likelihood of long-term post-detection survival. On the other hand, large scale screening could be prohibitively expensive, absent a easily-performed, low-cost test for mutations in the BRCA1 gene.

It as an object of the present invention to provide a screening methodology which can be used to provide low-cost testing for mutations in the BRCA1 gene.

It is a further object of the present invention to provide reagents, particularly primers and primer cocktails, which can be used in testing for mutations in the BRCA1 gene.

SUMMARY OF THE INVENTION

In accordance with the present invention, samples are tested for mutations in the BRCA1 gene using a hierarchical approach. First, each sample is amplified in one or more multiplex PCR amplification reactions. Each multiplex PCR reaction produces a mixture of amplified fragments. The sizes and amounts of these fragments are evaluated and compared to standard values reflecting the sizes and amounts of fragments produced when the same multiplex amplification is performed on the wild-type BRCA1 gene. Differences between the observed fragment sizes and/or amounts and those for the wild-type gene are indicative of a mutation with the BRCA1 gene of the sample.

The next step in the method of the invention is sequencing of one or more regions within the BRCA1 gene. In accordance with the hierarchical method, such sequencing will be performed on samples where no mutation was detected by analysis of the multiplex PCR fragments.

DETAILED DESCRIPTION OF THE INVENTION

Figure 1:
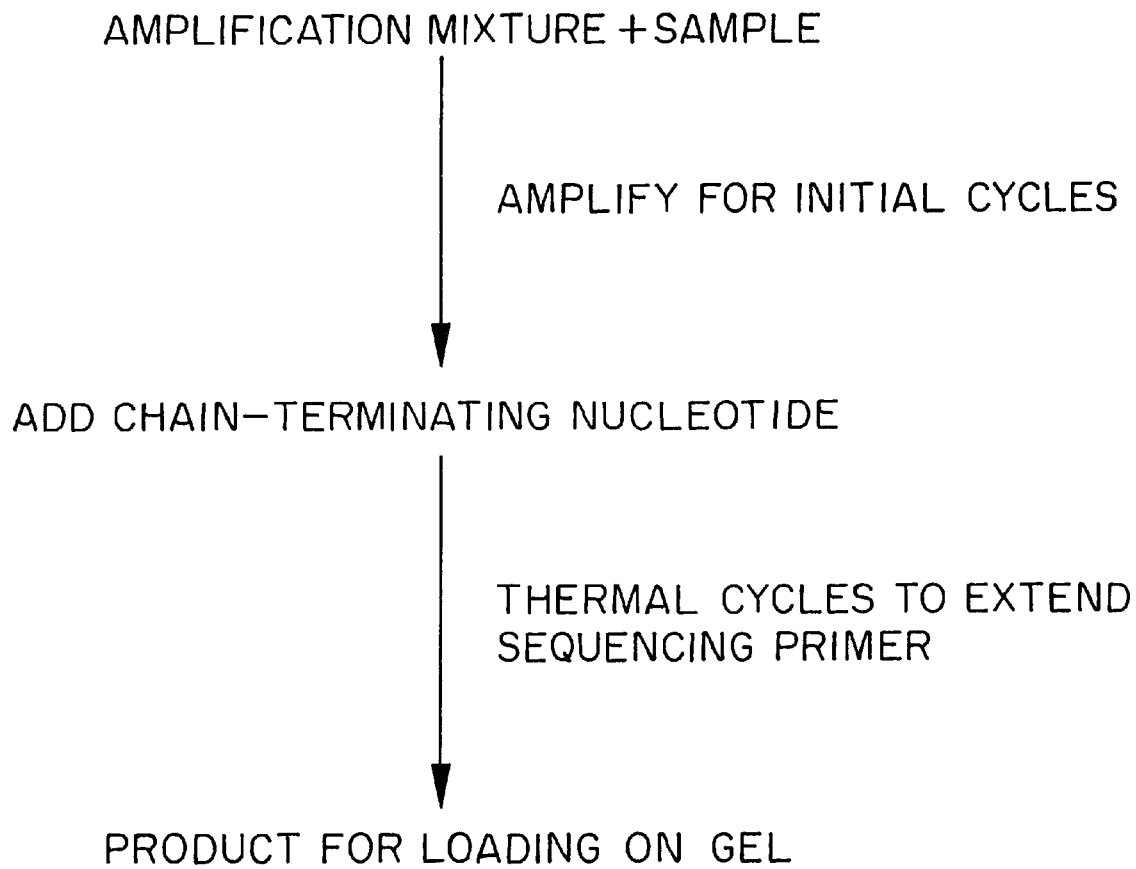
FIG. 1 illustrates an embodiment of the sequencing step of the method of the invention.

To date, over thirty BRCA1 mutations have been identified in the breast cancer families which have been studied. A substantial number of these mutations are insertion or deletion mutations. Furthermore, 75% of the currently known mutations are found in exon 11 and an additional 5% are found in exons 2 and 20. This type of distribution makes BRCA1 well-suited for analysis using the type of hierarchical analysis described in co-pending U.S. patent application Ser. No. 08/271,946 now U.S. Pat. No. 5,545,527. Use of a hierarchical analysis provides highly accurate test results at a reduced cost per patient.

The first step in the hierarchical analysis is multi-plex amplification and fragment length analysis of at least exons 2, 11 and 20 of the BRCA 1 gene. For multiplex amplification, a sample to be evaluated is combined with a several amplification primers. Amplification primers are selected to hybridize with the known sequence of the introns or exons of the BRCA1 gene. This sequence can be found online at the Breast Cancer Information Core, which has the following URL: http://www.nchgr.nih.gov/Intramural_research/Lab_transfer/Bic/. Information about the cDNA sequence can also be found from GenBank Accession No. U14680 or Genome Data Base Accession No. GDB: 126611. While considerable variation is theoretically possible in the sequence of these primers, the practical requirements for multiplex amplification and fragment analysis mean that primers cannot be simply selected at random. These requirements impose at least the following limitations on primers used in the method of the invention:

(1) in order to avoid the possibility of false positive results the primer pair, i.e., the combination of the 5'-primer and the 3'-primer for any given exon must be unique to the BRCA1 gene so that only the BRCA1 gene will be amplified. This means that the primer sequences will be generally somewhat longer than the minimum which can be used as an amplification primer. Preferred primers are from 18 to 23 nucleotides in length, without internal homology or primer-primer homology.

(2) It is also desirable for the primers to form more stable duplexes with the target DNA at the primers' 3'-ends than at their 5'-ends, because this leads to less false priming. Stability can be approximated by GC content, since GC base pairs are more stable than AT pairs, or by nearest neighbor thermodynamic parameters. Breslauer et al., "Predicting DNA duplex stability from base sequence", *Proc. Nat'l Acad. Sci. USA* 83: 3746–3750 (1986).

(3) To ensure complete amplification of each exon, the two primers of a pair are preferably selected to hybridize in the introns immediately flanking the exon to be amplified using the primer pair.

(4) Primer pairs are advantageously selected to have similar melting temperatures. Further, multiplex pools should contain primer pairs with approximately the same thermal profile, so that they can be effectively coamplified together. This goal can be achieved by having groups of primer pairs with approximately the same length and the same G/C content.

(5) The length of the gene region between the primer binding sites on a normal BRCA1 gene should be different for each exon to be multiplexed as a group. Differences of only one base in length are sufficient, provided a high resolution gel capable of resolving one base differences is used in analyzing the amplification products. However, greater differences in length are preferred, to avoid confusion in interpreting fragment sizes resulting from an insertion or deletion mutation.

Table 1 shows a series of amplification primers for various exons of the BRCA1 gene which meet these criteria when grouped into one of the multiplex groups as shown in the Table. It will be understood in the art that the same amplification products could be produced using primer pairs complementary to those set forth in Table 1. Because of the large size of exon 11, this exon is preferably amplified in multiple overlapping fragments using primers which bind to the exon in an interlocking manner so that all regions of the exon are amplified and analyzed, rather than using intron primers. This provides a more robust analysis, since amplification of shorter regions provides more reliable results, and also facilitates localization and identification of detected insertion or deletion mutations. Melting temperatures and optimum annealing temperatures in Table 1 are calculated assuming a salt concentration of 50 mM and 250 pM primer concentration. Conditions of actual use may be different, for example primer concentration of 200 nM to 1 μM will normally be used. Because of variations in primer and/or salt concentrations, experimental optimization using the calculated temperature as a starting point may be desirable.

While the foregoing set of primers provides the desirable ability to coamplify regions of the BRCA1 gene for fragment length analysis, it will be appreciated that other primers sets can be used as well based upon the known sequence of the BRCA1 gene by evaluating the uniqueness of the primer sequences and determining the predicted melting temperature for each primer. This can be accomplished in several ways. For example, the melting temperature, Tm can be calculated using either of the following equations:

$$Tm(^\circ C.)=81.5+16.6\times\log[Na]+0.41\times(\%GC)-675/length$$

where [Na] is the concentration of sodium ions, and the %GC is in number percent, or $$Tm(^\circ C.)=2\times(A+T)+4\times(G+C)$$

where A, T, G, and C represent the number of adenosine, thymidine, guanosine and cytosine residues in the primer. Alternatively, OLIGO™ software can be used to calculate Tm, nearest neighbor and ΔH/ΔG values. In general, primers for coamplification should be selected to have predicted melting temperatures differing by less than 4° C.

To perform the multiplex fragment analysis, each selected set of primers is combined with an aliquot of sample in a reaction mixture containing a template-dependant DNA polymerase, such as Taq polymerase, T7 DNA Polymerase, or Thermo Sequenase®; deoxynucleoside triphosphate feedstocks (A, C, G and T); and an appropriate buffer to permit extension of the primers. The resulting reaction mixture is thermally cycled through multiple cycles of annealing (performed at or below an average of the optimum annealing temperatures listed in Table 1), primer extension (performed at about 70 to 72° C.) and denaturation (performed at a temperature of around 95° C.). In practice, each reaction condition is optimized using the predicted temperatures as a starting points, and varying the temperature within a range from about 44 to 66° C.

After sufficient cycles to produce detectable levels of amplification products, the product mixture is loaded onto a separation matrix, e.g., a polyacrylamide gel, more specifically a PAGE sequencing gel, and separated on the basis of fragment size. Labeled amplification primers, particularly of amplification primers labeled with fluorophores such a fluorescein, facilitate detection of the separated bands within the separation matrix. The size of each detected fragment is determined, and compared to the expected size of the fragments for the multiplex amplification. Deviations in size or loss of a band reflect the presence and size of an insertion or deletion mutation involving the amplified fragment forming that band. Reduction in the intensity of a band generally reflects loss of one copy of the amplified exon or region in the sample.

The amplification reaction are preferably performed in a quantitative manner. This means that, for maximum effectiveness in the method of the present invention, the amplification of the exons in the sample should be carried out only for a number of cycles during which doubling of DNA is still being achieved.

Because of the frequency of insertion and deletion mutations among the known mutations in the BRCA1 gene, the fragment analysis test may, in many instances provide all the information that is needed to provide a diagnostic result. Where no insertion or deletion mutation is detected in the fragment analysis, however, the sample is further evaluated to determine the sequence of the one or more exons (or partial exons) of the BRCA1 gene.

Sequencing can be performed in known manner, although it will preferably be performed using a chain-termination sequencing reaction as originally described by Sanger et al. More preferably, the sequencing will be performed by amplification and sequencing of an exon (or portion thereof) of the BRCA1 gene using the methodologies disclosed in U.S. patent application Ser. No. 08/64,672 now U.S. Pat. No. 5,789,168 filed May 1, 1996, which is incorporated herein by reference. This amplification and sequencing procedure can be carried out on a fresh aliquot of the original sample, or on aliquots of one or more of the multiplex fragment analysis product mixtures.

FIG. 1 illustrates a first embodiment of the sequencing step of the present invention. As shown in FIG. 1, a sample containing a target nucleic acid polymer which is to be amplified and sequenced is combined with an amplification mixture containing two primers for an exon or portion of an exon of the BRCA1 gene, a mixture of dNTP's and thermostable polymerase in a buffer suitable for amplification. The primers may be the same primers as disclosed in Table 1, or other primers which hybridize selectively with the selected part of the BRCA1 gene.

The mixture is amplified through an initial set of cycles, for example 15–40 cycles. At this stage reagents for forming chain termination products, namely a dideoxynucleoside triphosphate (ddNTP) and optionally additional thermostable polymerase, dNTP's and a labeled sequencing primer are added and additional cycles (for example another 15–20 cycles) are performed during which both amplification and the formation of chain termination products occurs. The sequencing primer may be one of the primers disclosed in Table 1 for the exon or exon portion or some other primer which hybridizes specifically with the amplified portion of the BRCA1 gene, e.g., a nested primer. At the end of these cycles, the product mixture is evaluated to determine the lengths of the chain termination products, and hence the positions of the particular base corresponding to the ddNTP within the target nucleic acid polymer.

The thermostable polymerase used in at least the sequencing step of this amplification and sequencing process, and preferably in both steps, is one which incorporates dideoxynucleosides into an extending oligonucleotide at a rate which is no less than about 0.4 times the rate of incorporation of deoxynucleosides in the same amplification mixture. The commercially available enzyme Thermo Sequenase® is such an enzyme.

A variation of this method which may be advantageous is the use of asymmetric amplification to preferentially amplify one strand of the target nucleic acid. In this case, the primer which will produce the desired sequencing template strand is combined with the sample in an amount greater than the other primer, e.g., a 10 to 50-fold excess. More amplification cycles may be required to take full advantage of asymmetric amplification.

It may also be advantageous to biotinylate one of the primers used for amplification. When amplification is carried out with biotinylated primers, a partial separation of reagents can be accomplished prior to the introduction of the sequencing reagents by capturing the biotinylated amplification products on an avidin or streptavidin-coated support, separating the liquid medium from the support and replacing the liquid medium with the sequencing reagents. In a preferred use of this approach, the biotinylated products are captured on metal or magnetic beads, which are captured with a magnet to facilitate separation of the amplification liquid. While this step is not necessary to the method, and is not intended to accomplish complete removal of the amplification reagents, the use of this step can improve the sensitivity of the procedure by reducing the number of background oligonucleotides, particularly where a separate labeled-sequencing primer is added with the ddNTP.

Figure 2A:
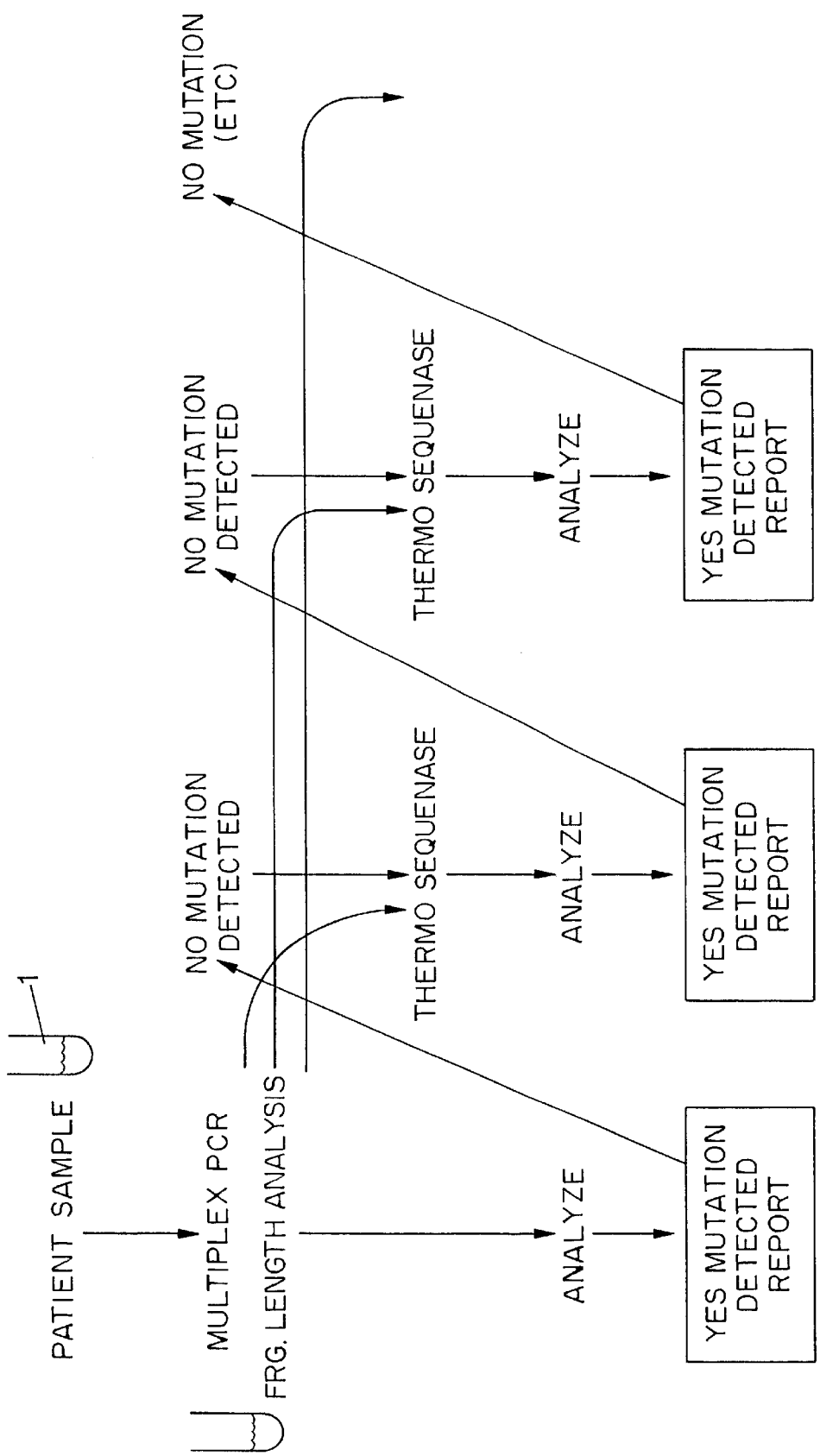
FIGS. 2A and 2B illustrate two embodiments of the method of the invention in which multiplex amplification and sequencing are performed sequentially on the same initial aliquot of sample.
Figure 2B:
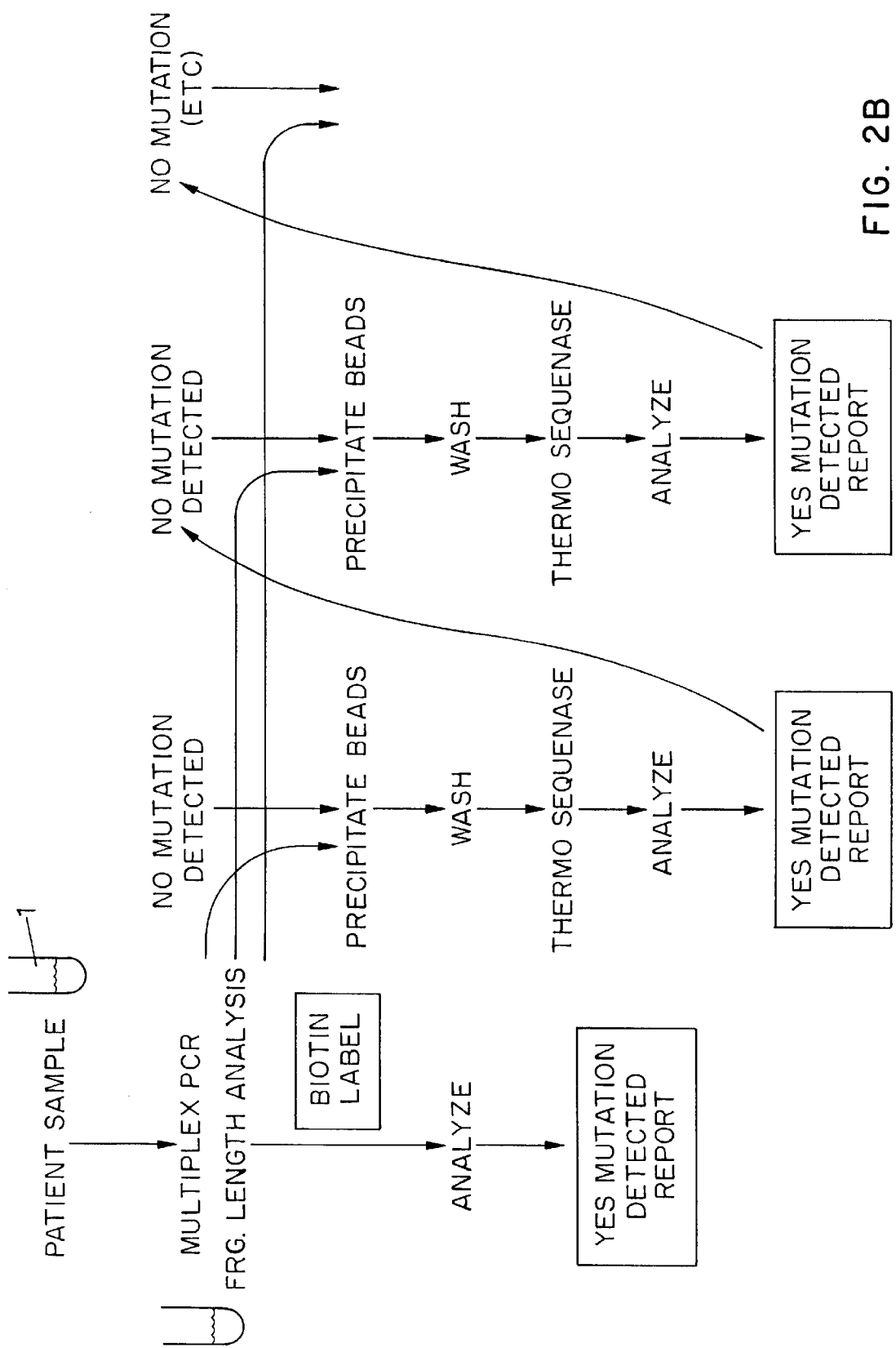

FIGS. 2A and 2B illustrate two embodiments of the method of the invention. As shown in FIGS. 2A and 2B, a patient sample 1 is first subjected to multiplex PCR to produce a complex mixture of amplification products using sets of amplification primers for the BRCA1 gene as disclosed in Table 1. The products of this mixture are analyzed, to detect insertion or deletion mutations. If the results of the fragment length analysis fail to show a mutation, the sample 1 is further analyzed by sequencing a selected exon or exons.

An aliquot of the original multiplex PCR amplification mixture is used as the starting material for multiple cycles of combined amplification and sequencing. Thus, the multiplex PCR amplification mixture is combined with amplification and/or labeled sequencing primers and amplified and sequenced in a single reaction vessel. Preferably, the multiplex amplification PCR is performed using capturable primers (for example biotin-labeled primers) and separated from the multiplex amplification reagents using affinity beads (e.g. avidin-coated beads) prior to the addition of the amplification/sequencing reagents. (FIG. 2B). Additional aliquots of the multiplex reaction mixture may be processed to sequence different regions if no mutation is detected in the first sequencing step.

It should be noted that the multiplex reaction performed in the first step of this embodiment makes use of labeled primers. Fluorescence from these primers may interfere with observation of a few peaks in the sequencing ladder. This interference can be minimized by utilizing a nested sequencing primer, which produces fragments having a maximum length which is shorter than the multiplex amplification products, or by the utilization of distinguishable labels for the multiplex amplification and sequencing primers.

The fragment analysis and sequencing steps of the present invention may also be advantageously combined with additional analytical steps for evaluation mutations in the BRCA1 gene. For example, a ligation analysis of the type described in the U.S. patent application Ser. No. 08/590,503 which is incorporated herein by reference can be used before or after the fragment length analysis to detect mutations in some or all of the exons of the BRCA1 gene. Briefly, this technique makes use of a set of oligonucleotide probes which hybridize in series along the length of the exon or region being evaluated. The ligation of the probes together forms a ligation product, the size of which is evaluated. When the gene or gene fragment being analyzed corresponds to the normal sequence and thus perfectly matches the probes, all of the probes in the set are ligated together, and the ligation product has a certain resulting size. When a mutation appears in the gene, the hybridization of the probe overlapping the mutation is impaired, with the result that some or all of the ligation product is of smaller size. By evaluating the size of the ligation product, both the existence of a mutation and its approximate position can be identified.

Use of CLEAVASE (Third Wave Technologies, Inc. Madison Wis.) provides another diagnostic technique which can be used according to the invention to identify mutations in BRCA1 by determining the sizes and amounts of amplified exon fragments. CLEAVASE is an endonuclease which cuts single stranded DNA (ssDNA) molecules. Since mutant ssDNA adopts a different conformation from wild-type ssDNA, the CLEAVASE digestion products show a different array of fragments. This array of fragments can be separated and examined by electrophoresis, much like multiplex PCR fragments. The advantage of CLEAVASE is that it can detect single base substitution mutations as well as insertions and deletions. Therefore, it detects fewer false negatives than multiplex PCR, though it does not locate mutations as precisely as sequencing.

TABLE 1

| Exon | Prod Size (bp) | Optimum Annealing Temp (° C.) | Seq. ID No. | Primer | Sense/Anti-sense | Tm (° C.) | MP P-1 |
|---|---|---|---|---|---|---|---|
| 1 | 234 | 59.1 | 1 | GGTAGCCCCTTGGTTTCCGTG | sense | 59.3 | A |
|   |     |      | 2 | ACGCCAGTACCCCAGAGCATC | anti  | 57.7 |   |
| 2 | 236 | 46.8 | 3 | AATGATGAAAATGAAGTTGTC | sense | 43.4 | B |
|   |     |      | 4 | GTTCATTTGCATAGGAGATAA | anti  | 44.1 |   |
| 2 | 275 | 47.7 | 75 | AAACCTTCCAAATCTTCAAAT | sense | 46.9 | C |
|   |     |      | 76 | TTCTGTTCATTTGCATAGGAG | anti  | 47.3 |   |
| 2 | 286 | 46.9 | 75 | AAACCTTCCAAATCTTCAAAT | sense | 46.9 | B |
|   |     |      | 77 | TGTAAGGTCAATTCTGTTCAT | anti  | 43.8 |   |

TABLE 1-continued

| Exon | Prod Size (bp) | Optimum Annealing Temp (° C.) | Seq. ID No. | Primer | Sense/Anti-sense | Tm (° C.) | MP P-1 |
|---|---|---|---|---|---|---|---|
| 3 | 116 | 47.3 | 5 | GAGCCTCATTTATTTTCTTTT | sense | 44.9 | C |
| | | | 6 | TGAAGGACAAAAACAAAAGCT | anti | 48.8 | |
| 4 | 204 | 49.2 | 7 | ACCTTAAATTTTTCAACAGCT | sense | 45.2 | E |
| | | | 8 | CTCTACAGAAAACACAAAATT | anti | 41.0 | |
| 5 | 202 | 46.6 | 9 | GCCTTTTGAGTATTCTTTCTA | sense | 43.2 | B |
| | | | 10 | TTCTACTTTTCCTACTGTGGT | anti | 42.8 | |
| 6 | 233 | 48.9 | 11 | AGGTTTTCTACTGTTGCTGCA | sense | 49.5 | D |
| | | | 12 | CAGCACTTCACTCTCATTCTT | anti | 46.1 | |
| 7 | 218 | 47.3 | 13 | CATACATTTTTCTCTAACTGC | sense | 41.5 | C |
| | | | 14 | GAAGAAGAAGAAAACAAATGG | anti | 45.5 | |
| 8 | 193 | 50.4 | 15 | AGGAGGAAAAGCACAGAACTG | sense | 50.4 | F |
| | | | 16 | TACTTAAAAAACCTGAGACCC | anti | 45.2 | |
| 9 | 197 | 46.0 | 17 | CAAGTACATTTTTTTAACCCT | sense | 43.2 | B |
| | | | 18 | AAAGAGAGAAACATCAATCCT | anti | 44.1 | |
| 10 | 227 | 48.9 | 19 | TTTGACAGTTCTGCATACATG | sense | 46.0 | D |
| | | | 20 | CAAATGGTCTTCAGAATAATC | anti | 43.4 | |
| 11a | 314 | 49.6 | 21 | CTCCAAGGTGTATGAAGTATG | sense | 44.0 | I |
| | | | 22 | CAGCCTTTTCTACATTCATTC | anti | 46.2 | |
| 11b | 348 | 49.8 | 23 | ATTACAGCATGAGAACAGCAG | sense | 47.2 | J |
| | | | 24 | GAGTCATCAGAACCTAACAGT | anti | 42.2 | |
| 11c | 340 | 49.1 | 25 | ATAGCAGCATTCAGAAAGTTA | sense | 44.2 | H |
| | | | 26 | TCAGTAACAAATGCTCCTATA | anti | 42.3 | |
| 11d | 314 | 50.2 | 27 | CTCCCCAACTTAAGCCATGTA | sense | 51.2 | K |
| | | | 28 | TCGAGTGATTCTATTGGGTTA | anti | 46.8 | |
| 11e | 325 | 49.2 | 29 | TGGTCATGAGAATAAAACAAA | sense | 45.1 | I |
| | | | 30 | TGGCATTTGGTTGTACTTTTT | anti | 49.4 | |
| 11f | 352 | 51.1 | 31 | AAGCCCACCTAATTGTACTGA | sense | 48.4 | L |
| | | | 32 | TTTGGGGTCTTCAGCATTATT | anti | 50.8 | |
| 11g | 307 | 48.3 | 33 | AAGAAGAGAAACTAGAAACAG | sense | 39.5 | H |
| | | | 34 | AATGGATACTTAAAGCCTTCT | anti | 44.3 | |
| 11h | 332 | 49.2 | 35 | AAGGGACTAATTCATGGTTGT | sense | 47.2 | I |
| | | | 36 | GTCTGTACAGGCTTGATATTA | anti | 41.5 | |
| 11i | 255 | 50.4 | 37 | TGAATGTGAACAAAAGGAAGA | sense | 47.4 | K |
| | | | 38 | ATGGGAAAAAGTGGTGGTATA | anti | 48.2 | |
| 11j | 346 | 48.6 | 39 | AACGAAACTGGACTCATTACT | sense | 45.0 | H |
| | | | 40 | TGTTTCTACCTAGTTCTGCTT | anti | 43.2 | |
| 11k | 340 | 49.4 | 41 | TGGGCTCCAGTATTAATGAAA | sense | 49.4 | I |
| | | | 42 | TCAGCAAAACTAGTATCTTCC | anti | 43.5 | |
| 11l | 313 | 49.8 | 43 | CATGCATCTCAGGTTTGTTCT | sense | 49.3 | J |
| | | | 44 | TATGCCTAGTAGACTGAGAAG | anti | 40.9 | |
| 11m | 312 | 52.7 | 45 | GCTTCCCTGCTTCCAACACTT | sense | 55.0 | L |
| | | | 46 | TGCCTCATTTGTTTGGAAGAA | anti | 52.5 | |
| 11n | 277 | 52.1 | 47 | ACAGTGCAGTGAATTGGAAGA | sense | 49.7 | K |
| | | | 48 | CTCCCCAAAAGCATAAACATT | anti | 50.5 | |
| 12 | 191 | 49.2 | 49 | GCGTTTATAGTCTGCTTTTAC | sense | 43.9 | E |
| | | | 50 | TTGGAGTGGTATTCTTTTAAG | anti | 43.7 | |
| 13 | 267 | 50.5 | 51 | TATTTCATTTTCTTGGTACCA | sense | 44.6 | F |
| | | | 52 | ATAAAGGGGAAGGAAAGAATT | anti | 47.9 | |
| 14 | 251 | 46.7 | 53 | GAATTATCACTATCAGAACAA | sense | 38.6 | B |
| | | | 54 | CAATCAGAGTTCAATATAAAT | anti | 38.3 | |

TABLE 1-continued

| Exon | Prod Size (bp) | Optimum Annealing Temp (° C.) | Seq. ID No. | Primer | Sense/Anti-sense | Tm (° C.) | MP P-1 |
|---|---|---|---|---|---|---|---|
| 15 | 393 | 47.4 | 55 | CCAGCAAGTATGAAATGTCCT | sense | 48.7 | C |
|    |     |      | 56 | CTTTATGTAGGATTCAGAGTA | anti | 38.3 |   |
| 16 | 559 | 49.6 | 57 | CTTAACAGAGACCAGAACTTT | sense | 42.4 | E |
|    |     |      | 58 | TTTCCAGAATGTTGTTAAGTC | anti | 43.9 |   |
| 17 | 212 | 48.5 | 59 | CTAGTATTCTGAGCTGTGTGC | sense | 44.3 | D |
|    |     |      | 60 | CCTCGCCTCATGTGGTTTTAT | anti | 53.3 |   |
| 18 | 258 | 48.9 | 61 | CTCTTTAGCTTCTTAGGACAG | sense | 42.8 | D |
|    |     |      | 62 | CTCAAGACTCAAGCATCAGCA | anti | 50.6 |   |
| 19 | 215 | 50.5 | 63 | TGTGAATCGCTGACCTCTCTA | sense | 50.0 | F |
|    |     |      | 64 | AAGTGGTGCATTGATGGAAGG | anti | 53.9 |   |
| 20 | 169 | 52.0 | 65 | TCTCTTATCCTGATGGGTGTG | sense | 49.0 | G |
|    |     |      | 66 | ATACAGAGTGGTGGGGTGAGA | anti | 50.8 |   |
| 21 | 167 | 56.4 | 67 | CAGTGGTGCGATCTCAGCTCA | sense | 56.2 | A |
|    |     |      | 68 | AAGGCTGGTGCTGGAACTCTG | anti | 55.8 |   |
| 22 | 273 | 51.0 | 69 | TAGAGGGCCTGGGTTAAGTAT | sense | 49.3 | G |
|    |     |      | 70 | GAGAAGACTTCTGACGCTACC | anti | 46.6 |   |
| 23 | 152 | 51.1 | 71 | CCTACTTTGACACTTTGAATG | sense | 44.3 | G |
|    |     |      | 72 | AATGTGCCAAGAACTGTGCTA | anti | 50.1 |   |
| 24 | 252 | 50.9 | 73 | TAATCTCTGCTTGTGTTCTCT | sense | 43.4 | F |
|    |     |      | 74 | GTAGCCAGGACAGTAGAAGGA | anti | 47.9 |   |

EXAMPLE 1

Individual exons of the BRCA1 gene are amplified as follows.

5 ul of patient sample genomic DNA (20 ng/ul) is combined with 2 ul 10×PCR Buffer, 0.6 ul 50 mM Mg2+, 0.4 ul 10 mM dNTP mix (containing each of the 4 dNTPs), 1 ul DMSO (100%), and 8 ul ddH20. 2 ul of a 50 ng/ul mixture of an amplification primer pair (i.e. 100 ng each primer), one of which is labeled with a detectable label, are added to the mix. The amplification primer pair is one of the pairs of exons designated in table 1 as being specific for a particular exon. A suitable label is fluorescein, which can be detected on an A.L.F. automated DNA sequencer (Pharmacia, Inc., Piscataway, N.J.).

The mixture is prepared on ice. Addition of 1 ul Taq Polymerase (1 U/ul) (Roche Molecular Systems, Inc.), bringing the total volume to 20 ul, is followed by thermal cycling as follows:

| Initial denaturation Cycle (20–35 times): | 94 C. | 10 min |
|---|---|---|
| anneal | *47 C. | 40 sec |
| extend | 72 C. | 60 sec |
| denature | 94 C. | 30 sec |
| Final extension temperature. | 72 C. | 10 min then hold at room |

*annealing temperature may vary within about 6° C. depending on empirically determined annealing temperature for the specific primer pair(s).

An equal volume of Stop Solution comprising Formamide and a visible dye is added after the reaction is complete. 6 ul of this mixture is loaded into a single lane of an A.L.F. Sequencing Gel, and the reaction products are detected.

EXAMPLE 2

Multiplex amplification of selected exons or parts of exons of BRCA1 is achieved as follows:

5 ul of patient sample genomic DNA (20 ng/ul) is combined with 2 ul 10×PCR Buffer, 0.6 ul 50 mM Mg2+, 0.4 ul 10 mM DNTP mix (containing equimolar amounts of each of the 4 dNTPs), 1 ul DMSO (100%), and 8 ul ddH20. 2 ul of a mixture containing 50 ng/ul of a multiplex set of primers as indicated in Table 1, (i.e. 100 ng each primer), one of each pair being labeled with a detectable label, are added to the mix. A suitable label is fluorescein, which can be detected on an A.L.F. automated DNA sequencer (Pharmacia, Inc., Piscataway, N.J.).

The mixture is prepared on ice. Addition of 1 ul Taq Polymerase (1 U/ul) (Roche Molecular Systems, Inc.), bringing the total volume to 20 ul, is followed by thermal cycling as follows:

| Initial denaturation Cycle (20–35 times): | 94 C. | 10 min |
|---|---|---|
| anneal | *47 C. | 40 sec |
| extend | 72 C. | 60 sec |
| denature | 94 C. | 30 sec |
| Final extension | 72 C. | 10 min then hold at room temperature. |

*annealing temperature may vary within about 6° C. depending on empirically determined annealing temperature for the specific primer pair (s).

An equal volume of Stop Solution comprising formamide and a visible dye is added after the reaction is complete. 6 ul of this mixture is loaded into a single lane of an A.L.F. Sequencing Gel, and the reaction products are detected.

EXAMPLE 3

Sequencing of an individual exon of BRCA1 is achieved as follows.

Amplified, biotinylated PCR product is prepared as a template for sequencing by generating the following mixture: 300 ng genomic DNA (patient sample); 1× Taq polymerase Buffer (final: 10 mM Tris-HCl, pH 8.3, 50 mM KCl, 1.5 mM MgC12, 0.001% gelatin); and 0.2 mM each dNTP. To this mixture is added 8 pMol of each primer selected from table 1 to amplify a specific exon of BRCA1, one of which primers is biotinylated. The reaction mixture is kept on ice until the addition of 2.5U Taq DNA polymerase. The final volume is 25 ul.

This reaction mixture is thermal cycled in a Perkin Elmer 9600 as follows:

| | |
|---|---|
| 94° C. 2 min | x1 cycle |
| 94° C. 30 sec | |
| *50° C. 30 sec | x35 cycles |
| 65° C. 2 min | |
| 65° C. 7 min | x1 cycle |

*annealing temperature may vary within about 6° C. depending on empirically determined annealing temperature for the specific primer pair(s).

At the end of the reaction, a 5 ul aliquot may be taken and observed on a 1% agarose gel containing ethidium bromide to assess integrity of the amplification reaction.

If the PCR product appears satisfactory, the reaction buffer is exchanged using streptavidin/magnetic beads as follows:
1. take 8 ul of streptavidin beads (Dynal), wash with 50 ul 2×BW buffer
2. resuspend beads in 10 ul of 2×BW buffer
3. remove 10 ul of PCR product from above and mix with washed beads.
4. sit at RT for up to 1 hour with periodic mixing by gently tapping side of tube.
5. place on magnetic rack, allow PCR bound-beads to separate and remove supernatant. Wash with 50 ul of 1×BW buffer, separate on magnetic rack and remove supernatant. Repeat with 50 ul of TE.
6. resuspend bound beads in 10 ul of dH20.
7. use 3 ul for cycle sequencing
*2×BW buffer: Binding/Washing buffer; 10 mM Tris pH 7.5, 1 mM EDTA, 2M NaCl The amplification products are then ready for sequencing as follows. A reaction mixture is prepared consisting of 2 ul T7. Thermo Sequenase™ buffer (Amersham Life Sciences, Cleveland) (final: 26 mM Tris-HCl, pH 9.5, 6.5 mM MgCl2); 3 ul of PCR product from above; 3ul (final: ~30 ng/5 pM) Fluoresceinated primer; 3 ul dH20; and 2 ul diluted Thermo Sequenase™ enzyme (Amersham Life Sciences, Cleveland) (final 6.4 U). The total volume of 13 ul is kept on ice.

The fluoresceinated primer used has the same sequence as the non-biotinylated primer used in the amplification reaction, above, but it is fluoresceinated so that it may be detected on an A.L.F. Automated DNA Sequencing Apparatus (Pharmacia, Inc.; Piscataway, N.J.)

The reagents are mixed well, and a 3 ul aliquot is added to each of the 4 termination reaction tubes containing 3 ul of Termination Mix. The final volume of 6 ul is covered with 10 ul mineral oil before thermal cycling.

The d/ddA Termination mix contains 750 uM dNTPs, 2.5 uM ddATP.

The d/ddC Termination mix contains 750 uM dNTPs, 2.5 uM ddCTP.

The d/ddG Termination mix contains 750 uM dNTPs, 2.5 uM ddGTP.

The d/ddT Termination mix contains 750 uM dNTPs, 2.5 uM ddTTP.

The sequencing reactions are then thermal cycled in a Perkin Elmer 9600 as follows:

| | |
|---|---|
| 94° C. 2 min | x1 cycle |
| 94° C. 30 sec | |
| *50° C. 10 sec | cycle 25 times |
| 70° C. 30 sec | |
| 70° C. 2 min | x1 cycle |

*annealing temperature may vary within about 6° C. depending on empirically determined optimization for the specific amplification primer.

After the cycle sequencing reaction is complete, 6 ul of STOP buffer comprising dextran blue in formamide is added to the reaction mixture. 6 ul or half of the reaction products are loaded onto an A.L.F. Sequencer.

EXAMPLE 4

Single-Tube Sequencing of a BRCA1 exon may be achieved as follows.

The primer pair is selected from table 1 and is specific for the designated exon of BRCA1. Asymmetric amplification of the sequencing template strand is obtained using an excess ratio (10–50 fold) of template strand primer compared to the non-template strand primer. The following reactants were combined in an Eppendorf tube at 4 degrees C. in the following amounts:

300 ng patient sample genomic DNA
Primer 1: 1 pmole
Primer 2: 20 pmole
1×Thermo Sequenase™ buffer (Amersham Life Sciences, Cleveland) (final: 26 mM Tris-HCl, pH 9.5, 6.5 mM MgCl2)
5% DMSO
0.2 mM dNTPS (i.e. 0.05 of each dATP, dCTP, dGTP, dTTP)
0.25 units Thermo Sequenase™ enzyme (Amersham Life Sciences, Cleveland)

Final reaction volume: 4 microlitres. This small volume allowed for the reaction to proceed close to completion, and particularly to consume available dNTPs during the amplification step. The reaction was overlaid with 10 microlitres of Chill Out Liquid Wax.

The reaction tube was place in a Perkin-Elmer 9600 Thermo-Cycling apparatus and thermal cycled as follows:

| | |
|---|---|
| 94° C. 2 min | x1 cycle |
| 94° C. 30 sec | |
| *60° C. 30 sec | x39 cycles |
| 72° C. 2 min | |
| 65° C. 7 min | x1 cycle |

*annealling temperature may vary within about 6° C. depending on empirically determined optimization for the specific primer pair.

After thermal cycling, the reaction vessel was cooled to 4 C. for 10 min, whereupon the Chill Out Wax solidified and prevented any PCR carry over of product which could lead to contamination.

6 microliters of the following sequencing mix was then added:
1.2 microliters: Sequencing Primer (20 pmole)
1.0 microliters concentrated Thermo Sequenase™ buffer (Amersham
Life Sciences, Cleveland) (final: 26 mM Tris-HCl, pH 9.5, 6.5 mM MgCl2)

1.0 microliters thermal stable polymerase (Thermo Sequenase) (3 units)
1.0 microliters 20% (v/v) DMSO
3.0 microliters 1:100 ratio of ddNTP and 4 dNTPs (final concentrations of 2.5 microM and 250 microM respectively).

The Sequencing primer selected was a fluoresceinated version of the subservient primer (i.e. the one originally added in lesser amount). The fluorescent label allows for detection of reaction products in an automated DNA sequencer, such as the Pharmacia A.L.F.

The ddNTP selected corresponds to the desired termination reaction, and is either ddATP, ddCTP, ddGTP or ddTTP.

The reaction was thermal cycled at the following temperatures in a Perkin-Elmer 9600 thermal cycling apparatus for 15 cycles
95° C. 15 sec
50° C. 5 sec
70° C. 15 sec After the thermal cycles, the reaction was cooled to 4 C. It was mixed with 6 microliters stop solution (formamide and glycerol), and 1–3 (up to 10) microliters were loaded per lane of an A.L.F. automated sequencer.

EXAMPLE 5

Multiplex amplification of fragments of exon 11 listed in Table 1 as fragments 11b, 11d, 11i and 11l, of BRCA1 was achieved as follows:

5 ul of patient sample genomic DNA (20 ng/ul) was combined with 2 ul 10×PCR Buffer, 0.6 ul 50 mM Mg2+, 0.4 ul 10 mM DNTP mix (containing each of the 4 dNTPs), 1 ul DMSO (100%), and 6 ul ddH20. 1 ul of a mixture containing 50 ng/ul of each primer pair (indicated in Table 1), (i.e. 50 ng each primer), one of each pair being labeled on its 5' end with a fluorescein label, was added to the mix, totaling 4 ul (1 ul for each primer pair).

The mixture was prepared on ice. Addition of 1 ul Taq Polymerase (1 U/ul) (Roche Molecular Systems, Inc.), brought the total volume to 20 ul, and was followed by thermal cycling as follows:

| Initial denaturation | 94 C. | 10 min |
| --- | --- | --- |
| Cycle (20–35 times): | | |
| anneal | 50 C. | 40 sec |
| extend | 72 C. | 60 sec |
| denature | 94 C. | 30 sec |

Final extension 72 C. 10 min then held at room temperature.

An equal volume of Stop Solution comprising formamide and a visible dye was added after the reaction was completed. 6 ul of this mixture was loaded into a single lane of an A.L.F. Sequencing Gel, and the reaction products were detected on an A.L.F. automated DNA sequencer (Pharmacia, Inc., Piscataway, N.J.).

EXAMPLE 6

The procedure of Example 2 is repeated, using a combination of primers identified by Sequence ID Nos. 3, 4, 65 and 66 to perform a multiplex amplification of exons 2 and 20.

---

We claim:

1. A method for testing a sample for mutations in the BRCA1 gene comprising the steps of:
   (a) amplifying exons 1 and 21, or a portion of each exon, of the BRCA1 gene to produce amplified fragments, wherein the exons or portions thereof are amplified in a multiplex amplification reaction to produce multiplex amplification products for analysis;
   (b) determining the sizes and amounts of amplified fragments in the multiplex amplification products and comparing the determined sizes or amounts to standard values for amplification of the same exons or portions thereof of wild-type BRCA1 gene, wherein a difference in fragment size or amount is indicative of the presence of a mutation in the BRCA1 gene; and
   (c) if no mutation is detected in the BRCA1 gene as a result of the determination of the sizes and amounts of the amplification fragments, determining the sequence of one or more exons of the BRCA1 gene.

2. The method according to claim 1, wherein exons 1 and 21 or the portions thereof are amplified using the primers identified by Sequence ID Nos. 1, 2, 67 and 68.

3. A method for testing a sample for mutations in the BRCA1 gene comprising the steps of:
   (a) amplifying exons 2, 5, 9 and 14, or a portion of each exon, of the BRCA1 gene to produce amplified fragments, wherein the exons or portions thereof are amplified using the primers identified by Sequence Nos. 3, 4, 9, 10, 17, 18, 53 and 54 in a multiplex amplification reaction to produce multiplex amplification products for analysis;
   (b) determining the sizes and amounts of amplified fragments in the multiplex amplification products and comparing the determined sizes or amounts to standard values for amplification of the same exons or portions thereof of wild-type BRCA1 gene, wherein a difference in fragment size or amount is indicative of the presence of a mutation in the BRCA1 gene; and
   (c) if no mutation is detected in the BRCA1 gene as a result of the determination of the sizes and amounts of the amplification fragments, determining the sequence of one or more exons of the BRCA1 gene.

4. A method for testing a sample for mutations in the BRCA1 gene comprising the steps of:
   (a) amplifying exons 3, 7 and 15, or a portion of each exon, of the BRCA1 gene to produce amplified fragments, wherein the exons or portion thereof are amplified using the primers identified by Sequence Nos. 5, 6, 13, 14, 55 and 56 in a multiplex amplification reaction to produce multiplex amplification products for analysis;
   (b) determining the sizes and amounts of amplified fragments in the multiplex amplification products and comparing the determined sizes or amounts to standard values for amplification of the same exons or portion thereof of wild-type BRCA1 gene, wherein a difference in fragment size or amount is indicative of the presence of a mutation in the BRCA1 gene; and
   (c) if no mutation is detected in the BRCA1 gene as a result of the determination of the sizes and amounts of the amplification fragments, determining the sequence of one or more exons of the BRCA1 gene.

5. A method for testing a sample for mutations in the BRCA1 gene comprising the steps of:
   (a) amplifying exons 6, 10, 17 and 18, or a portion of each exon, of the BRCA1 gene to produce amplified fragments, wherein the exons or portions thereof are amplified in a multiplex amplification reaction to produce multiplex amplification products for analysis;
   (b) determining the sizes and amounts of amplified fragments in the multiplex amplification products and comparing the determined sizes or amounts to standard values for amplification of the same exons or portions thereof of wild-type BRCA1 gene, wherein a difference in fragment size or amount is indicative of the presence of a mutation in the BRCA1 gene; and
   (c) if no mutation is detected in the BRCA1 gene as a result of the determination of the sizes and amounts of the amplification fragments, determining the sequence of one or more exons of the BRCA1 gene.

6. The method according to claim 5, wherein exons 6, 10, 17 and 18 or portions thereof are amplified using the primers identified by Sequence ID Nos. 11, 12, 19, 20, 59, 60, 61 and 62.

7. A method for testing a sample for mutations in the BRCA1 gene comprising the steps of:
   (a) amplifying exons 4, 12 and 16, or a portion of each exon, of the BRCA1 gene to produce amplified fragments, wherein the exons or portions thereof are amplified in a multiplex amplification reaction to produce multiplex amplification products for analysis;

(b) determining the sizes and amounts of amplified fragments in the multiplex amplification products and comparing the determined sizes or amounts to standard values for amplification of the same exons or portions thereof of wild-type BRCA1 gene, wherein a difference in fragment size or amount is indicative of the presence of a mutation in the BRCA1 gene; and (c) if no mutation is detected in the BRCA1 gene as a result of the determination of the sizes and amounts of the amplification fragments, determining the sequence of one or more exons of the BRCA1 gene.

8. The method according to claim 7, wherein exons 4, 12 and 16 or portions thereof are amlplified using the primers identified by Sequence ID Nos. 7, 8, 49, 50, 57 and 58.

9. A method for testing a sample for mutations in the BRCA1 gene comprising the steps of:

(a) amplifying exons 8, 13, 19 and 24, or a portion of each exon, of the BRCA1 gene to produce amplified fragments, wherein the exons or portions thereof are amplified in a multiplex amplification reaction to produce multiplex amplification products for analysis;

(b) determining the sizes and amounts of amplified fragments in the multiplex amplification products and comparing the determined sizes or amounts to standard values for amplification of the same exons or portions thereof of wild-type BRCA1 gene, wherein a difference in fragment size or amount is indicative of the presence of a mutation in the BRCA1 gene; and (c) if no mutation is detected in the BRCA1 gene as a result of the determination of the sizes and amounts of the amplification fragments, determining the sequence of one or more exons of the BRCA1 gene.

10. The method according to claim 9, wherein exons 8, 13, 19 and 24 or portions thereof are amplified using the primers identified by Sequence ID Nos. 15, 16, 51, 52, 63, 64, 73 and 74.

11. A method for testing a sample for mutations in the BRCA1 gene comprising the steps of:

(a) amplifying exons 20, 22 and 23, or portion of each exon, of the BRCA1 gene to produce amplified fragments, wherein the exons or portions thereof are amplified in a multiplex amplification reaction to produce multiplex amplification products for analysis;

(b) determining the sizes and amounts of amplified fragments in the multiplex amplification products and comparing the determined sizes or amounts to standard values for amplification of the same exons or portions thereof of wild-type BRCA1 gene, wherein a difference in fragment size or amount is indicative of the presence of a mutation in the BRCA1 gene; and (c) if no mutation is detected in the BRCA1 gene as a result of the determination of the sizes and amounts of the amplification fragments, determining the sequence of one or more exons of the BRCA1 gene.

12. The method according to claim 11, wherein exons 20, 22 and 23 or portions thereof are amplified using the primers identified by Sequence ID Nos. 65, 66, 69, 70, 71 and 72.

13. A method for testing a sample for mutations in the BRCA1 gene comprising the steps of:

(a) amplifying exons 2 and 20, or a portion of each exon, of the BRCA1 gene to produce amplified fragments, wherein the exons or portions thereof are amplified using the primers identified by Sequence Nos. 3, 4, 65 and 66 in a multiplex amplification reaction to produce multiplex amplification products for analysis;

(b) determining the sizes and amounts of amplified fragments in the multiplex amplification products and comparing the determined sizes or amounts to standard values for amplification of the same exons or portions thereof of wild-type BRCA1 gene, wherein a difference in fragment size or amount is indicative of the presence of a mutation in the BRCA1 gene; and (c) if no mutation is detected in the BRCA1 gene as a result of the determination of the sizes and amounts of the amplification fragments, determining the sequence of one or more exons of the BRCA1 gene.

14. A kit for testing a sample for mutations in the BRCA1 gene comprising a mixture of at least four oligonucleotide primers, said primers being selected to amplify exons 1 and 21, or a portion of each exon, of the BRCA1 gene in a multiplex amplification reaction.

15. The kit according to claim 14, wherein the primers for amplification of exons 1 and 21 are the primers identified by Sequence ID Nos. 1, 2, 69 and 70.

16. A kit for testing a sample for mutations in the BRCA1 gene comprising a mixture of at least four oligonucleotide primers, said primers being selected to amplify exons 2, 5, 9 and 14, or a portion of each exon, of the BRCA1 gene in a multiplex amplification reaction, wherein the primers used for amplification are the primers identified by Sequence ID Nos. 3, 4, 9, 10, 17, 18, 55 and 56.

17. A kit for testing a sample for mutations in the BRCA1 gene comprising a mixture of at least four oligonucleotide primers, said primers being selected to amplify exons 3, 7 and 15, or a portion of each exon, of the BRCA1 gene in a multiplex amplification reaction, wherein the primers used for amplification are the primers identified by Sequence ID Nos. 5, 6, 13, 14, 57 and 58.

18. A kit for testing a sample for mutations in the BRCA1 gene comprising a mixture of at least four oligonucleotide primers, said primers being selected to amplify exons 6, 10, 17 and 18, or a portion of each exon, of the BRCA1 gene in a multiplex amplification reaction.

19. The kit according to claim 18, wherein the primers for amplification of exons 6, 10, 17 and 18 are the primers identified by Sequence ID Nos. 11, 12, 19, 20, 61, 62, 63 and 64.

20. A kit for testing a sample for mutations in the BRCA1 gene comprising a mixture of at least four oligonucleotide primers, said primers being selected to amplify exons 4, 12 and 16, or a portion of each exon, of the BRCA1 gene in a multiplex amplification reaction.

21. The kit according to claim 20, wherein the primers for amplification of exons 4, 12 and 16 are the primers identified by Sequence ID Nos. 7, 8, 51, 52, 59 and 60.

22. A kit for testing a sample for mutations in the BRCA1 gene comprising a mixture of at least four oligonueleotide primers, said primers being selected to amplify exons 8, 13, 19 and 24, or a portion of each exon, of the BRCA1 gene in a multiplex amplification reaction.

23. The kit according to claim 22, wherein the primers for amplification of exons 8, 13, 19 and 24 are the primers identified by Sequence ID Nos. 15, 16, 53, 54, 65, 66, 75 and 76.

24. A kit for testing a sample for mutations in the BRCA1 gene comprising a mixture of at least four oligonucleotide primers, said primers being selected to amplify exons 20, 22 and 23, or a portion of each exon, of the BRCA1 gene in a multiplex amplification reaction.

25. The kit according to claim 24, wherein the primers for amplification of exons 20, 22 and 23 are the primers identified by Sequence ID Nos. 67, 68, 71, 72, 73 and 74.

26. A kit for testing a sample for mutations in the BRCA1 gene comprising a mixture of at least four oligonucleotide primers, said primers being selected to amplify exons 2 and 20, or a portion of each exon, of the BRCA1 gene in a multiplex amplification reaction, wherein the primers used for amplification are the primers identified by Sequence ID Nos. 3, 4, 65 and 66.

27. An oligonucleotide primer having the sequence as set forth in any one of Sequence ID Nos. 1 through 77.

* * * * *